ns Patent [19]

Fukui et al.

[11] 4,195,129
[45] Mar. 25, 1980

[54] METHOD FOR IMMOBILIZING ENZYMES AND MICROBIAL CELLS

[75] Inventors: Saburo Fukui, Nagaokakyo; Tsutomu Yamamoto; Takamitsu Iida, both of Hiratsuka, all of Japan

[73] Assignee: Kansai Paint Co., Ltd., Japan

[21] Appl. No.: 865,433

[22] Filed: Dec. 29, 1977

Related U.S. Application Data

[63] Continuation-in-part of Ser. No. 700,562, Jun. 28, 1976, abandoned, and Ser. No. 700,577, Jun. 28, 1976, abandoned.

[30] Foreign Application Priority Data

Nov. 26, 1975 [JP] Japan ................................. 50-140839
Nov. 26, 1975 [JP] Japan ................................. 50-140840

[51] Int. Cl.² ............................................. C07G 7/02
[52] U.S. Cl. ..................................................... 435/182
[58] Field of Search .................. 195/63, 68, DIG. 11, 195/59; 204/159.16

[56] References Cited

U.S. PATENT DOCUMENTS

| | | | |
|---|---|---|---|
| 3,788,950 | 1/1974 | Hicks et al. | 195/DIG. 11 X |
| 3,859,169 | 1/1975 | O'Driscoll et al. | 195/63 |
| 3,860,490 | 1/1975 | Guttag | 195/59 X |
| 3,968,016 | 7/1976 | Wismer | 204/159.16 |

*Primary Examiner*—David M. Naff
*Attorney, Agent, or Firm*—Ostrolenk, Faber, Gerb & Soffen

[57] ABSTRACT

A method for immobilizing enzymes or microbial cells which comprises the steps of uniformly mixing an aqueous dispersion of enzymes or microbial cells with a photo-curable resin having a number average molecular weight of 800 to 100,000, two or more photopolymerizable ethylenically unsaturated groups per molecule and hydrophilic groups, and irradiating actinic rays to the above mixture of photo-curable resin and enzymes or microbial cells. The immobilized product is advantageously used in various enzymatic reactions with stable enzyme activity.

10 Claims, No Drawings

METHOD FOR IMMOBILIZING ENZYMES AND MICROBIAL CELLS

CROSS-REFERENCE TO RELATED APPLICATION

This application is a continuation-in-part of copending applications Ser. No. 700,562 and Ser. No. 700,577, both filed on June 28, 1976 respectively, and both now abandoned.

BACKGROUND OF THE INVENTION

This invention relates to a method for immobilizing enzymes or microbial cells. More particularly, the invention relates to a method for preparing immobilized enzymes or microbial cells which can be easily shaped and prepared by using hydrophilic photo-curable resin having two or more photopolymerizable ethylenically unsaturated groups per molecule.

In order to minimize the instability of enzyme activity and to facilitate continuous enzymatic reaction processes, the technique of immobilizing enzymes and using them as a solid catalyst has been recently developed in several industrial fields.

As methods for preparing the immobilized enzyme, there are an adsorption method, covalent bond method, cross-linking method and entrapping method. In the last-mentioned entrapping method, the enzyme itself is not bound to any matrix but it is entrapped or micro-encapsulated in fine lattice of gel. Therefore, the activity of entrapped enzyme can be well maintained and thus various kinds of enzymes and microbial cells are treated by this method. In order to put this method into practive, however, it is necessary to select a suitable immobilizing material which entraps enzymes or microbial cells therein without causing release and has selective permeability to the substrate.

In the conventional entrapping method, an aqueous suspension of enzymes or microbial cells is first well mixed with low molecular weight hydrophilic monomers such as acrylamide, hydroxyethyl acrylate, hydroxyethyl methacrylate, hydroxypropyl acrylate and hydroxypropyl methacrylate, and the mixture is then immobilized as it stands by polymerization. However, in this method, it is difficult to properly control the selective permeability of the obtained polymer matrix, so that the entrapped enzymes or microbial cells are liable to be released from the polymer matrix. In addition, toxicity of the immobilized product is apprehended when it is used in the food industry and the pharmaceutical industry because unreacted low molecular weight monomers remain in the reaction product. Further, there is also well known an entrapping method (for example, U.S. Pat. No. 3,860,490) which comprises mixing the micro-organisms with an aqueous or organic solution of a polymer and then cross-linking the polymeric matrix to entrap the micro-organisms. In this method using the polymer solution, the toxicity problem can be settled. However, it is difficult to properly control the selective permeability of the polymer matrix.

BRIEF SUMMARY OF THE INVENTION

It is accordingly the primary object of the present invention to provide a novel method for preparing improved immobilized enzymes or microbial cells having various advantageous features.

Another object of the present invention is to provide immobilized enzymes or microbial cells which are useful and economical from an industrial view point since the activity of enzyme can be made stable and the entrapped enzymes or microbial cells are well retained in the polymer matrix.

A further object of the present invention is to provide novel immobilized enzymes or microbial cells which can be shaped into any desired configurations and has no toxicity.

The inventors of the present invention have found that the drawbacks of the prior art process, namely the toxicity problem and the control of selective permeability problem, can be eliminated if an aqueous suspension of the enzymes or microbial cells is mixed with the following hydrophilic resin and then polymerized by actinic ray irradiation. It was further found that it was possible to uniformly control the selective permeability of the resin matrix when the photopolymerization is effected only when the resin had two or more photopolymerizable ethylenically unsaturated groups per molecule.

According to the method of the present invention, an aqueous suspension of enzymes or microbial cells and hydrophilic resin is mixed well and formed into a desired shape, and then it is polymerized by irradiating actinic rays of 2500 to 6000 Å in wave length. The hydrophilic resin is characterized by having a number average molecular weight of 800 to 100,000, preferably 1000 to 70,000, by having two or more of photopolymerizable ethylenically unsaturated groups per molecule and by having hydrophilic groups.

DETAILED DESCRIPTION OF THE INVENTION

In accordance with the present invention, the molecular weight of the photo-curable resin is previously adjusted so as to pass substrates but not to release entrapped enzymes or microbial cells, and the photo-curable resin is cured by irradiating actinic rays for a short period of time in a single step operation to produce a mechanically stable immobilized product. It is desired that the photo-curable resin has hydrophilic groups to the extent that the resin uniformly mixes with the aqueous solution such as buffer solution containing the suspension of enzymes or microbial cells when they are immobilized. The activity of enzymes or microbial cells can be thus maintained in a most stable condition and the enzymes or microbial cells are immobilized without the loss of their activity. Further, in contrast to the methods employing gamma rays or electron beams, degradation of the activity of enzymes or microbial cells is not caused to occur during the curing step since the above defined actinic rays are used in the method of this invention.

In order to immobilize enzymes or microbial cells, two or more photopolymerizable ethylenically unsaturated groups are necessary for each molecule of the photo-curable resin. Further, when the number average molecular weight of the photo-curable resin is lower than 800, the cured product is liable to become brittle because the linearity of cross-linkage is low, and on the other hand, when the number average molecular weight of the photo-curable resin is higher than 100,000, the viscosity of the mixture of photo-curable resin and the suspension of enzymes or microbial cells becomes too high and the workability of resin is impaired. Therefore, the number average molecular weight of the photo-curable resin should be within the range of 800 to 100,000, and preferably from 1,000 to 70,000.

It has been understood that the following advantages can be expected over the conventional methods when the enzymes or microbial cells are immobilized by the method of the present invention, that is, the photo-curable resin having hydrophilic groups is prepared previously from low molecular weight monomers, and the next step, the mixture of the photo-curable resin and the aqueous suspension of enzymes or microbial cells (hereinafter referred to as "enzyme-resin composition") is cured by the irradiation of actinic rays. The dimensions of vacant spaces of the obtained polymer lattice can be freely controlled and the liberation of enzymes or microbial cells can be satisfactorily prevented, which gives an economical advantage. When the photo-curable resin is cured by gamma rays or electron beams, the activity of enzyme contained in the resin composition is degraded because the energy of gamma rays or electron rays is very strong, however, in the method of the present invention, such disadvantage is not caused to occur since ultraviolet rays or visible rays are employed to cure the enzyme-resin composition. Therefore, in view of this fact, the activity of enzymes or microbial cells can also be maintained well.

Furthermore, the skeletal structure of the resin is previously formed and the enzyme-resin composition is then cured by a short time irradiation of actinic rays, and therefore, the lowering of the activity of enzymes or microbial cells can be prevented, which is desirable as compared with the case when the polymers are prepared directly from low molecular weight monomers through relatively longer irradiation. Still further, the steps of mixing the suspension of enzymes or microbial cells are photo-curable resin and irradiating actinic rays are very simple and easy and in addition, low molecular weight monomers generally having toxicity are not handled, and therefore, the working environment in the preparation process can be much improved. When enzymes or microbial cells are immobilized by using low molecular weight monomers as in the conventional method, the enzymes or microbial cells coexist with remaining monomers, so that the monomers must be removed through severe conditions of heating, acid or alkali treatment or organic solvent treatment. Thus, the activity of enzymes or microbial cells is seriously degraded by such treatments. In the method of the present invention, however, the remaining monomer can be easily eliminated in the step of producing the photo-curable resin, that is, in the step before the mixing of enzymes or microbial cells. Therefore, the product prepared according to the method of the present invention can be safely used in the food industry and pharmaceutical industry in which the toxicity of remaining monomer has become an issue. Further, there is another advantage in that the work of formation or molding of immobilized products is carried out without difficulty because the curing is done by the irradiation for short time and the photo-curable resin is viscous to some extent. When the enzymes or microbial cells are formed into a membrane or a film, another resin can be mixed together into the photo-curable resin composition in order to improve the mechanical strength of the film product or strong bonds may be previously introduced into the molecules of photo-curable resin. Therefore, the mechanical strength of the immobilized enzymes or microbial cells can be freely controlled. As the case may be, the photo-curing resin solution containing enzymes or microbial cells is impregnated into or applied over synthetic or natural substances as substrates and they are then cured by the irradiation of actinic rays.

As a photo-curable resin having hydrophilic groups, there are ones having nonionic hydrophilic groups and ones having ionic hydrophilic groups. In this invention, the photo-curable resin having nonionic groups may be used alone or preferably in admixture with the photo-curable resin having ionic groups. The combined use of the photo-curable resin having ionic groups brings durable activity of enzymes or microbial cells of increased operative stability which is based on the ionic bond between ionic hydrophilic groups and enzymes or microbial cells. The compounding ratio of the resin having ionic hydrophilic groups to the resin having nonionic hydrophilic groups is in the range of 1/99 to 50/50 by weight, preferably 3/97 to 20/80 by weight. When the amount of resin having ionic groups is more than above defined range, the photo-curability of the resin composition becomes poor because the ionic groups of the resin molecules orient outward into the water phase to form the surface of resin molecules, while the hydrophobic hydrocarbon units having ethylenically unsaturated groups are encased, so that the resins can not photo-cure enough to retain the enzyme or microbial cells in polymer matrix. On the other hand, when the amount of the resin having ionic groups is less than above defined range, durable enzyme or microbial activity of increased operative stability is not expected.

As disclosed in the above, the photo-curable resin having ionic hydrophilic groups is used in the specified amount together with the photo-curable resin having nonionic hydrophilic groups, so that when the immobilized product is used for continuous enzymatic reaction of a substrate containing foreign substances such as ionic pigments, an ion exchange reaction is caused to occur simultaneously with the enzymatic reaction. Therefore, the step for eliminating pigment can be omitted and the reaction process can be improved. In addition to the above-mentioned ion exchange reaction, a simultaneous molecular sieve effect can be obtained by controlling the cross-linking density of the resin, and thus, the immobilized product of the present invention is of wide use. Further, it is cured by using actinic rays so that it can be produced at low cost as compared with the conventional methods.

The photo-curable resins having nonionic hydrophilic groups to be used in the present invention are exemplified in the following.

Polyesters made from polyethylene glycol and acrylic or methacrylic acid:
diesters of unsaturated monocarboxylic acid made from acrylic or methacrylic acid and polyethylene glycol of 400 to 10,000 in molecular weight containing less than 30% by weight of propylene oxide group; esterified products of unsaturated monocarboxylic acid made from 2 moles of acrylic or methacrylic acid and 1 mole of polyethylene glycol of 600 to 10,000 in molecular weight; and esterified products of unsaturated monocarboxylic acid made from n moles of unsaturated acid such as maleic anhydride, n+1 moles of polyethylene glycol having a molecular weight of 600 to 10,000 and 2 moles of unsaturated monocarboxylic acid such as acrylic acid and methacrylic acid.

Urethanated adducts of polyethylene glycol and 2-hydroxyethyl acrylate or methacrylate:
urethanated products made from n moles of diisocyanate such as tolylene diisocyanate, xylene diisocyanate, isophorone diisocyanate and hexamethylene diisocyanate, n−1 moles of polyethylene glycol having a molecular weight of 800 to 10,000 and 2 moles of unsaturated monohydroxy compound such as 2-hydroxyethyl acrylate or methacrylate; and urethanated products made from n moles of triisocyanate such as Desmodur L (trademark of Farbenfabriken Bayer A.G.), n−1 moles of polyethylene glycol having a molecular weight of 800 to 10,000 and n+2 moles of 2-hydroxyethyl acrylate or methacrylate.

Unsaturated cellulose:
adduct of water soluble celluloses such as cellulose acetate phthalate, hydroxypropylmethyl cellulose phthalate and hydroxyethyl cellulose with unsaturated glycidyl compounds such as glycidyl acrylate and glycidyl methacrylate; and reaction products of water soluble celluloses with N-methylol acrylic amide using acidic catalyst.

Unsaturated polyvinyl alcohol:
unsaturated polyvinyl alcohol made from polyvinyl alcohol and N-methylol acrylamide by using acidic catalyst.

Unsaturated polyamide:
unsaturated polyamide made from adding the adduct of 1 mole of diisocyanates such as tolylene diisocyanate and xylene diisocyanate and 1 mole of unsaturated hydroxyl compound such as 2-hydroxyethyl acrylate, to water soluble polyamide such as gelatine.

On the other hand, photo-curable resins having ionic hydrophilic groups such as carboxyl, sulfonic, phosphatic and amino groups which are used in combination with the above mentioned resins having nonionic hydrophilic groups are as follows:

Salts of high acid value unsaturated polyesters:
Salts of unsaturated polyesters having acid values of 40 to 200 which are obtained by esterification of polyhydric alcohols with polycarboxylic acid components consisting of at least one unsaturated polycarboxylic acid such as maleic anhydride, maleic acid, fumaric acid, itaconic acid and itaconic anhydride and at least one saturated polycarboxylic acid such as trimellitic acid, trimellitic anhydride, pyromellitic acid and pyromellitic anhydride; unsaturated polyesters having acid values of 40 to 200 which are obtained by allowing acid anhydride to react with the hydroxyl groups of esterified products which are prepared from at least one unsaturated polycarboxylic acid such as maleic anhydride, maleic acid, fumaric acid, itaconic acid and itaconic anhydride and polyhydric alcohol containing more than 5% by weight of tri- or higher-hydric alcohol; and unsaturated polyesters having acid values of 40 to 200 which are obtained by allowing unsaturated glycidyl compounds such as glycidyl acrylate and glycidyl methacrylate to react with the carboxyl groups of reaction products which are prepared by allowing saturated polycarboxylic acids such as trimellitic acid and trimellitic anhydride to react with terminal hydroxyl groups of esterified products comprising saturated dibasic acids such as adipic acid, phthalic acid and phthalic anhydride and glycols such as ethylene glycol, propylene glycol and 1,3-butylene glycol.

Unsaturated epoxides with high acid values:
unsaturated epoxides having acid values of 40 to 200 which are prepared by adding acid anhydride to the remaining hydroxyl groups of addition products made from n moles of glycidyl group in polyglycidyl compounds such as Epikote 828, 1001 and 1004 (trademark, made by Shell Chemical Co., Ltd.) having glycidyl groups, n−1 moles of carboxyl group in dicarboxylic acids such as maleic acid and adipic acid and 2 moles of unsaturated carboxylic acids such as acrylic acid and methacrylic acid; and unsaturated epoxides having acid values of 40 to 200 which are prepared by the reaction between unsaturated glycidyl compounds such as glycidyl acrylate and glycidyl methacrylate and the compound obtained by adding acid anhydride to the remaining hydroxyl groups of the addition product made from n moles of glycidyl group in polyglycidyl compound and n+1 moles of carboxyl group in dicarboxylic acid.

Anionic unsaturated acrylic resins:
The anionic unsaturated acrylic resins herein referred to are copolymers of acrylic or methacrylic acid and acrylic or methacrylic esters which meet the following equation (1) and other conditions:

$$C + 5P + 10S = A \qquad (1)$$

in which C is the concentration (mol/kg) of carboxyl groups in the resin, P is the concentration (mol/kg) of phosphatic groups in the resin and S is sulfonic groups (mol/kg) in the resin. A of equation (1) is 0.8 to 5 (mol/kg) and the concentration of photopolymerizable ethylenically unsaturated groups in the resin is 0.1 to 5 (mol/kg). The preparation of the copolymer of acrylic or methacrylic acid and acrylic or methacrylic ester is performed according to the conventional method. In order to introduce carboxyl groups into resin, unsaturated carboxylic compounds such as acrylic or methacrylic acid is used as copolymer components. The phosphatic groups are introduced by using unsaturated phosphate esters such as Phosmer M and Phosmer Cl (trademarks, made by Yushi Seihin Co., Ltd. in Japan) and sulfonic groups, unsaturated sulfonate esters such as 2-sulfoethyl acrylate or methacrylate and 3-sulfopropyl acrylate or methacrylate. In order to introduce photopolymerizable ethylenically unsaturated groups into the resin, unsaturated glycidyl compound such as glycidyl acrylate or methacrylate is allowed to react with carboxyl groups, phosphatic groups or sulfonic groups contained in the resin.

Cationic unsaturated acrylic resins:
unsaturated acrylic resin made by the reaction between unsaturated glycidyl compound such as glycidyl acrylate or methacrylate and copolymer of methacrylic esters containing more than 5% by weight of unsaturated amino compounds such as 2-diethylaminoethyl acrylate or methacrylate, tert-butylaminoethyl acrylate or methacrylate and vinylpyridine; unsaturated acrylic resin that is made by chloromethylating polystyrene and quaternizing the product with unsaturated amino compound; and the adduct made from polyethylene imine and unsaturated glycidyl compound.

Unsaturated polyamines:
polyamines made from n moles of polyethylene glycol diglycidyl ether having a molecular weight of 500 to 10,000, n+1 moles of one or more amine compounds selected from alkyl amines such as butyl amine and diamines such as hexamethylene diamine and 2 moles of unsaturated glycidyl compounds such as glycidyl acrylate and glycidyl methacrylate.

Unsaturated carboxylated cellulose:
adduct of water soluble cellulose such as cellulose acetate phthalate, hydroxypropylmethyl cellulose phthalate and hydroxyethyl cellulose with unsaturated acid anhydrides such as itaconic anhydride and maleic anhydride.

The method of the present invention can be applied to various kinds of enzymes and microbial cells and the activity of them are maintained at high ratio after they are immobilized. In the following, several enzymes and microbial cells are exemplified, however, it is to be noted that they are non-restrictive examples with regard to the present invention.

Enzymes:
urease, glucose oxidase, catalase, glucoamylase, glucose isomerase, invertase, acetoacetic decarboxylase, glucose oxidase-catalase, peroxidase, lactase, D-amino acid oxidase, α-galactosidase, aminoacylase, aspartase and penicillin amidase.

Microbial cells:
those of *Lactobacillus bulgaricus, Aerobacter aerogenes, Bacillus subtilis, Azotobacter vinelandii* and *Proteus vulgaris*.

In order to promote the photopolymerization of the method of the present invention, commonly known photosensitizers are added to enzyme-resin composition. Examples include α-carbonyl alcohols such as benzoin and acetoin; acyloin ethers such as benzoin methyl ether, benzoin ethyl ether, benzoin isopropyl ether, anisoin ethyl ether and pivaloin ethyl ether; α-substituted acyloins such as α-methylbenzoin and α-methoxybenzoin; naphthol; hydroxyanthracene; azoamide such as 2-cyano-2-butyl azoformamide; uranyl nitrate; ferric chloride; mercaptan; disulfide; ascorbic acid and rivoflavin. The above compounds can be advantageously used, however, mercaptans, disulfides, halogenides and dyestuffs are also used.

In the working of the method of the present invention, the enzyme-resin composition is first formed into a desired shape and actinic rays are then irradiated to the shaped composition so as to cure it. If the actinic rays reach the composition to be cured, the composition may be formed into any desired shape and thickness with or without a container. Further, the composition can be applied on the surfaces of articles, laminated on other materials, charged in transparent containers, impregnated into porous materials, or allowed to flow freely with irradiation. The articles to be applied with this composition may be any of natural or synthetic products including knitted or woven cloths, metallic products and the like.

As the light source of actinic rays for irradiation, any instrument that gives out light rays in the range of 2500 to 6000 Å in wave length can be used. Exemplified as such light sources are low pressure mercury lamps, high pressure mercury lamps, fluorescent lamps, xenon lamps, carbon arc lamps and sun light. The irradiation time is generally from 1 minute to 10 minutes. It is advisable to irradiate light rays in an atmosphere of inert gas so as to reduce the irradiation time.

In order that those skilled in the art may better understand the present invention and the manner in which it may be practiced, the following specific examples are given. In the examples, unless otherwise indicated, parts and percents are by weight.

EXAMPLE 1

A uniform mixture was prepared from 90 parts of NK Ester 23G (trademark of dimethacrylate of polyethylene glycol having a molecular weight of 1000, made by Shin Nakamura Chemical Ind. Ltd. in Japan), 10 parts of 0.5% aqueous solution of glucose oxidase (containing catalase) dissolved in 0.1 M phosphate buffer solution at pH 5.6, and 1 part of benzoin ethyl ether. A platinum electrode was immersed into thus prepared mixed solution and the electrode carrying the mixed solution thereon was irradiated at a temperature below 25° C. for 5 minutes by a low pressure mercury lamp from the directions around the electrode, thus an electrode covered by immobilized enzyme was formed. The above-mentioned electrode and another lead electrode as an opposite electrode were immersed in a 0.1% glucose solution and electrical measurement was carried out, as the result, the response of electrodes caused by glucose was observed.

EXAMPLE 2

Photo-curable resin (number average molecular weight: 2160) was prepared from 1 mole of xylene diisocyanate, 750 g of polyethylene glycol having a molecular weight of 1500 and 1.1 mole of 2-hydroxyethyl methacrylate. Further, 85 parts of the thus prepared photo-curable resin, 15 parts of 0.1% buffer solution of urease, and 2 parts of benzoin methyl ether were uniformly mixed together. A glass plate of 3 mm in thickness, on which a square frame (5 cm×5 cm in inner dimensions) was formed with spacers of 1 mm in thickness was horizontally placed and the above obtained mixture was poured into the inner frame on the glass plate. On the mixed solution, a polyester sheet of 0.5 mm in thickness was closely placed. It is then irradiated at temperature below 35° C. for 2 minutes by a 2 KW high pressure mercury lamp which is placed at a distance of 5 cm above, thereby forming a transparent immobilized enzyme product. This enzyme film was rinsed thrice with respective 200 ml of distilled water and immersed in 100 ml of 0.01 M urea solution prepared with 0.01 M phosphate buffer solution. The urea was allowed to react for 30 minutes at 30° C. Then 5 ml of reaction solution was taken out and, after adding 5 ml of 0.1 N-HCl to the solution, it was subjected to back-titration with 0.1 N-NaOH. As the result of this test, it was understood that the ratio of activity to that of native enzyme was 68%.

EXAMPLE 3

Photo-curable resin (number average molecular weight: 2160) was prepared from 1 mole of xylene diisocyanate, 750 g of polyethylene glycol having a molecular weight of 1500 and 1.1 mole of 2-hydroxyethyl methacrylate. Further, 65 parts of this photo-curable resin, 20 parts of NK Ester M-9G (trademark of methacrylate of methoxypolyethylene glycol having a molecular weight of 400, made by Shin Nakamura Chemical Ind. Ltd.), 1 part of benzoin ethyl ether and 15 parts of the solution prepared by dispersing 100 mg of glucose isomerase in 100 ml of buffer solution, were mixed together uniformly.

A glass-made test tube of 19 mm in outer diameter was concentrically placed in another glass-made test tube of 22 mm in inner diameter and the above mixed solution was poured in the space between the test tubes. Irradiation was then conducted at temperature below 35° C. for 3 minutes by using four 500 W high pressure mercury lamps from four directions perpendicular to the longitudinal walls of the test tubes, thereby obtaining a tubular transparent solid product. This tubular product was filled with 10 ml of 2% glucose-phosphate buffer solution containing magnesium ions and cobalt ions, and kept at 50° C. The liquid which permeated through the tubular film was collected and the color was developed by the cysteine-carbazole method so as to measure the formation of fructose by colorimetry at 560 mμ in wave length. As the result, it was understood that 43% of glucose was converted into fructose.

EXAMPLE 4

An enzyme solution was prepared by adding 50 mg of glucoamylase and 50 mg of glucose isomerase to 10 ml of buffer solution at pH 7.0 and to this enzyme solution were uniformly added 90 g of NK Ester 23G (used in Example 1) and 1 g of benzoin ethyl ether. The above mixture was then poured into the inner frame used in Example 2 and 0.2 mm thick polyester film was closely placed on the mixture. From the above film, irradiation was carried out at temperature below 35° C. for 1 minute by using a low pressure mercury lamp placed at 10 cm distance above to obtain a immobilized enzyme film. This enzyme film was cut into plural pieces of 1 cm square and they were rinsed thrice with 100 ml of buffer solution. The cut pieces were then immersed into 100 ml of 2% maltose solution containing magnesium ions and cobalt ions (pH: 7.0) as substrate and it was allowed to react for 60 minutes at 45° C. The produced fructose was analyzed by the cysteine-carbazole method and it was understood that the ratio of activity to that of native enzyme was 45%.

EXAMPLE 5

A uniform mixture was prepared from 90 parts of NK Ester 23G (used in Example 1), 10 parts of *Proteus vulgaris* microbial cells suspended in 0.1 M phosphate buffer solution at pH 7.0, and 1 part of benzoin methyl ether. This mixture was applied to a piece of gauze to form a 0.5 mm thick film and then, a 0.3 mm thick transparent polyester sheet was placed thereon. It was then irradiated at temperature below 25° C. for 3 minutes by a low pressure mercury lamp placed at 5 cm distance above and after the irradiation, the polyester sheet was peeled off to obtain a immobilized product of microbial cells containing the gauze as supporting structure.

EXAMPLE 6

Photo-curable resin having nonionic hydrophilic groups (number average molecular weight: about 2500) was prepared from 1 mole of xylene diisocyanate, 1000 g of polyethylene glycol having a molecular weight of 2000 and 1 mole of 2-hydroxyethyl methacrylate. Further, photo-curable resin having ionic hydrophilic groups (number average molecular weight: about 1500) was prepared by allowing 2 moles of glycidyl methacrylate to react with the reaction product which was obtained by allowing 2 moles of trimellitic anhydride to react with the esterified product prepared from 3 moles of adipic acid and 4 moles of 1,3-butylene glycol.

Then, a uniform mixture was prepared from 97 parts of the former nonionic resin, 3 parts of the latter ionic resin, 2 parts of benzoin ethyl ether and 300 parts of aqueous solution of enzymes made by dissolving 3.5 g of glucose oxidase and 0.35 g of peroxidase into 1000 ml of phosphate buffer solution at pH 7.0.

This mixture was poured into the inner frame on the polyester film of 0.2 mm in thickness, on which square frame (20 cm×20 cm in inner dimension) was formed with spacers of 1 mm in thickness and was horizontally placed. A polyester film of 0.2 mm in thickness was closely placed over the mixture and irradiation was carried out at temperature below 35° C. for 10 seconds by using a 2 KW high pressure mercury lamp placed at 10 cm distance above, thereby forming a film of immobilized enzyme.

This enzyme film was rinsed trice with 1000 ml of buffer solution and cut into plural pieces of 1 cm square. The 5 pieces of the cut film were then immersed into 10 ml of a solution made by dissolving 2 g of glucose and 0.05 g of O-diamisidine into 1000 ml of buffer solution (pH: 7.0) and it was allowed to react for 10 minutes at 30° C. Afterwards, color measurement of the solution was done by colorimetry at 420 mμ in wave length to show 1.5 times activity of the immobilized enzyme which was obtained by using nonionic type photo-curable resin alone.

EXAMPLE 7

83 parts of unsaturated polyamide made by adding an adduct of 1 mole of tolylene diisocyanate and 1 mole of 2-hydroxyethyl acrylate to a water-soluble polyamide having a molecular weight of 1000, 17 parts of photo-curable resin prepared from 1 mole of trimellitic acid, 6000 g of polyethylene glycol having a molecular weight of 3000 and 2 mole of acrylic acid, 2 parts of benzoin ethyl ether and 300 parts of aqueous solution of enzymes made by dissolving 3.5 g of glucose oxidase and 0.35 g of peroxidase into 1000 ml of phosphate buffer solution at PH 7.0, were uniformly mixed together.

This mixture was applied in the same manner as in Example 6 and a film of immobilized enzyme was obtained. The activity of the immobilized enzyme was then measured by the same manner as in Example 6. As the result, it was understood that an activity equal to that of Example 6 was obtained.

EXAMPLE 8

95 parts of nonionic photo-curable resin (number average molecular weight: about 3704) made from 1500 g of polyethylene glycol having a molecular weight of 3000, 1 mole of isophorone diisocyanate and 1 mole of 2-hydroxyethyl methacrylate, 5 parts of cationic photo-curable resin (number average molecular weight: about 2563) made from 2060 g of polypropylene glycol diglycidylether having a molecular weight of 1030, 3 moles of butyl amine and 2 moles of glycidyl methacrylate, 2 parts of benzoin isopropyl ether and 300 parts of acetoacetic decarboxylase aqueous solution made by dissolving 0.5 g of it into 1000 ml of phosphate buffer solution at pH 6, were uniformly mixed together.

This mixture was applied in the same manner as in Example 6 and a film of immobilized enzyme was obtained. The activity of the immobilized enzyme was then measured by Warburg constant volume manometer. As the result, it was understood that 1.2 times activity was obtained as compared with that of the immobilized enzyme which was obtained by using nonionic type photo-curable resin alone and in addition, operative stability of the immobilized enzyme was increased.

EXAMPLE 9

In 100 parts of a 20% aqueous solution of water soluble unsaturated cellulose prepared from the reaction of 1000 g of hydroxypropyl methyl cellulose having a molecular weight of 15,000 and 1 mole of N-methylol acrylamide in acidic aqueous solution of phosphoric acid were added 1 part of cationic photo-curable resin made from 2 moles of Desmodur L (trademark of Bayer A.G.), 7500 g of polyethylene glycol having a molecular weight of 7500, 3 moles of 2-hydroxyethyl methacrylate and 1 mole of 2-dimethyl aminoethanol and 0.5 part of polypropylene glycol (a molecular weight: 2000) dissolved 10% of benzoin therein and pH of the obtained mixture was adjusted to 6. Then, 300 parts of the same acetoacetic decarboxylase aqueous solution as in Example 8 was added to the mixture and they were uniformly mixed.

This mixture was applied in the same manner as in Example 6 and a film of immobilized enzyme was obtained. The activity of the immobilized enzyme was then measured by Warburg constant volume manometer. As the result, it was understood that 1.2 times activity was obtained as compared with that of the immobilized enzyme which was obtained by using nonionic type photo-curable resin alone and in addition, operative stability of the immobilized enzyme was increased.

EXAMPLE 10

Photo-curable resin having nonionic hydrophilic groups was prepared by allowing to react an aqueous solution comprising 100 parts of 10% aqueous solution of polyvinyl alcohol (molecular weight: 70,000, rate of saponification: 90%), 2 parts of N-methylol acrylamide and 0.1 part of phosphoric acid for 5 hours at 60° C. and then neutralizing the reaction product with caustic soda. Further, photo-curable resin having ionic hydrophilic groups was prepared by allowing 2 moles of succinic anhydride to react with the reaction product which was obtained by allowing 1 mole of polypropylene glycol diglicidylether to react with 2 moles of acrylic acid.

Then, a uniform mixture was prepared from 40 parts of the former nonionic resin, 10 parts of the latter ionic resin, 10 parts of polypropylene glycol (molecular weight: 2000) having dissolved 10% of benzoin therein and 10 parts of acylase aqueous solution made by dissolving 0.5 g of acylase into 10 ml of phosphate buffer solution.

This mixture was applied in the same manner as in Example 6 except that irradiation was carried out for 3 minutes and a film of immobilized enzyme was obtained. This enzyme film was cut into plural pieces of 1 cm square. The 10 pieces of the cut film were then immersed into 10 ml of 50 mM N-acetyl-DL-methionine prepared by dissolving it in phosphate buffer solution at pH 7.5, and allowed to react for 30 minutes at 37° C. After the reaction, L-methionine yield was measured by the ninhydrin method. As the result, it was understood that the ratio of activity to that of native acylase was 70%.

COMPARATIVE EXAMPLE 1

A solution of 10 g of a dry hydroxyethyl methacrylate homopolymer (a molecular weight: about 8000) in 85 g of ethylene glycol monomethyl ether was prepared. A solution of 0.2 g of ammonium dichromate in 5 ml distilled water was then added and the solution was mixed during 5 minutes to produce a cross-linkable hydroxyethyl methacrylate polymer solution.

An aqueous solution of 1.0 g of glucose oxidase and 0.2 g of peroxidase in 300 ml of phosphate buffer solution at pH 7.0 was prepared, and 5 g of this solution was mixed with 45 g of the above polymer solution.

On a horizontal polyethylene film, a 0.2 mm thick layer of the mixture was cast. A flow of cold dry nitrogen was directed toward the surface of the film during 5 minutes. The film was then irradiated for 10 minutes with a 2 KW high pressure mercury lamp placed 10 cm above the surface to cross-link the polymer, thereby forming a film of immobilized enzyme. The activity of the immobilized enzyme was then measured by the same manner as in Example 6. As the result, it was understood that the ratio of the activity to that of the immobilized enzyme of Example 6 was 10%.

What is claimed is:

1. A method for immobilizing enzymes or microbial cells which is characterized in the steps of:
    uniformly mixing aqueous dispersion of enzymes or microbial cells with a monomer-free photo-curable resin having a number average molecular weight of 800 to 100,000, two or more photo-polymerizable ethylenically unsaturated groups per molecule and nonionic hydrophilic groups; and
    irradiating actinic rays having a wave length of 2500 to 6000 Å to said mixture, whereby said enzymes or microbial cells are entrapped in said resin.

2. A method for immobilizing enzymes or microbial cells as claimed in claim 1 wherein said mixture additionally contains another monomer-free photo-curable resin having a number average molecular weight of 800 to 100,000, two or more photo-polymerizable ethylenically unsaturated groups per molecule and ionic hydrophilic groups, the ratio of the resin having ionic hydrophilic groups to the resin having nonionic hydrophilic groups being in the range of 1/99 to 50/50 by weight.

3. A method for immobilizing enzymes or microbial cells as claimed in claim 2, wherein said enzymes are urease, glucose oxidase, catalase, glucoamylase, glucose isomerase, invertase, acetoacetic decarboxylase, glucose oxidase-catalase, peroxidase, lactase, D-amino acid oxidase, α-galactosidase, aminoacylase, aspartase or penicillin amidase, and said microbial cells are the cells of *Lactobacillus bulgaricus, Aerobacter aerogenes, Bacillus subtilis, Azotobacter vinelandii* or *Proteus vulgaris.*

4. A method for immobilizing enzymes or microbial cells as claimed in claim 2, wherein said photo-curable resin having ionic hydrophilic groups is at least one member selected from the group consisting of: salts of high acid value unsaturated polyesters, high acid value unsaturated epoxides, anionic unsaturated acrylic resins, cationic unsaturated acrylic resins, unsaturated polyamines and unsaturated carboxylated cellulose.

5. A method for immobilizing enzymes or microbial cells as claimed in claim 2, wherein said photo-curable resin having nonionic hydrophilic groups is at least one member selected from the group consisting of: polyesters made from polyethylene glycol and acrylic or methacrylic acid, urethanated adduct of the product made from polyisocyanate and polyethylene glycol with 2-hydroxyethyl acrylate or methacrylate, unsaturated cellulose, unsaturated polyvinyl alcohol and unsaturated polyamide.

6. A method for immobilizing enzymes or microbial cells as claimed in claim 2, wherein said ratio is in the range of 3/97 to 20/80 by weight.

7. A method for immobilizing enzymes or microbial cells as claimed in claim 2, wherein a photosensitizer is added to said mixture of photo-curable resins.

8. A method for immobilizing enzymes or microbial cells as claimed in claim 7, wherein said photosensitizer is at least one member selected from the group consisting of α-carbonyl alcohol, acyloin ether, α-substituted acyloin, naphtol, hydroxyanthracene, axoamide, uranyl nitrate, ferric chloride, mercaptan, disulfide, ascorbic acid and rivoflavin.

9. A method for immobilizing enzymes or microbial cells as claimed in claim 2, wherein said number average molecular weight is 1,000 to 70,000.

10. A method for immobilizing enzymes or microbial cells as claimed in claim 4, wherein said high acid value is 40 to 200.

* * * * *